United States Patent [19]

Hester, Jr.

[11] 4,264,615
[45] Apr. 28, 1981

[54] COMPOSITIONS AND PROCESS
[75] Inventor: Jackson B. Hester, Jr., Galesburg, Mich.
[73] Assignee: The Upjohn Company, Kalamazoo, Mich.
[21] Appl. No.: 81,743
[22] Filed: Oct. 4, 1979

Related U.S. Application Data

[63] Continuation of Ser. No. 924,973, Jul. 17, 1978, abandoned, which is a continuation-in-part of Ser. No. 309,213, Nov. 24, 1972, which is a continuation-in-part of Ser. No. 138,288, Apr. 28, 1971, and a continuation-in-part of Ser. No. 201,207, Nov. 22, 1971, said Ser. No. 201,207, is a continuation-in-part of Ser. No. 138,278, Apr. 28, 1971.

[51] Int. Cl.³ ............................................. A61K 31/41
[52] U.S. Cl. ................................................... 424/269
[58] Field of Search ............................... 424/273, 269

Primary Examiner—Stanley J. Friedman
Attorney, Agent, or Firm—John J. Killinger

[57] ABSTRACT

Pharmaceutical compositions comprising, in unit dosage form, from about 0.5 mg. to about 100 mg. of a compound of the formula:

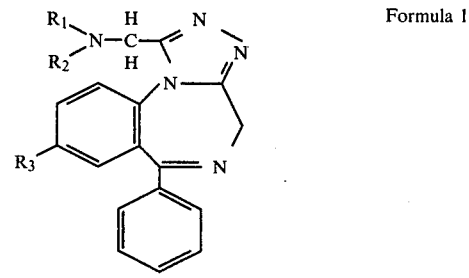

Formula I wherein $R_1$ and $R_2$ are hydrogen, methyl or ethyl, and $R_3$ is hydrogen, fluorine, chlorine, bromine, —CN, —$NO_2$, —$CF_3$, or alkylthio in which the alkyl is from one to three carbon atoms, inclusive; including the pharmacologically acceptable acid addition salts or H-oxides thereof, in association with a pharmaceutical carrier. The process is the administration of the above compositions to humans at a dose of from about 0.1 mg./kg./day to about 1 mg./kg./day for anti-depressant and anti-anxiety effects.

17 Claims, No Drawings

COMPOSITIONS AND PROCESS

CROSS REFERENCE TO RELATED APPLICATIONS

This is a continuation, of application Ser. No. 924,973, filed July 17, 1978, now abandoned, which is a continuation-in-part of application Ser. No. 309,213, filed Nov. 24, 1972, which in turn is a continuation-in-part of application Ser. No. 138,288, filed Apr. 28, 1971, and of application Ser. No. 201,207, filed Nov. 22, 1971. Application Ser. No. 201,207 itself is a continuation-in-part of application Ser. No. 138,278, filed Apr. 28, 1971.

BRIEF SUMMARY OF THE INVENTION

This invention is a therapeutic composition for treating humans and animals comprising a benzodiazepine of the Formula 1 and including the pharmacologically acceptable acid addition salts or N-oxides thereof in combination with a pharmaceutical carrier and a method for treatment of conditions requiring antidepressant and/or anxiolytic (antianxiety) medication.

DETAILED DESCRIPTION OF THE INVENTION

The compounds of the Formula 1 can be prepared by methods disclosed in copending application Ser. No. 309,213, filed Nov. 24, 1972.

The compounds of the Formula 1 unexpectedly show both anti-depressive and anti-anxiety activities. They can be used when prepared in unit dosage forms, in association with a pharmaceutical carrier for treatment of both depression or anxiety as well as mixed states of anxiety and depression such as occur in certain neurosis, sometimes referred to as the anxiety-depression syndrome.

The compositions of the present invention are presented for systemic administration to humans and animals in unit dosage form and can be administered orally, parenterally, and rectally.

For oral administration either solid or fluid unit dosage forms can be prepared. For preparing solid compositions such as tablets, the compound of Formula 1 is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Wafers are prepared in the same manner as tablets, differing only in shape and the inclusion of sucrose or other sweetener and flavor. In their simplest embodiment, capsules, like tablets, are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared with a syrup vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

For rectal administration a compound of the Formula 1 in the form of a suppository is preferred and is prepared by compounding with a solid which melts at body temperature, e.g., cocoa butter or a solid which is miscible in body fluids, e.g., polyethylene glycol. Similarly, solutions which are adapted for use as retention enemas can be prepared.

The term unit dosage form as used in the specification and claims refers to physically discrete units suitable as unitary dosages for human subjects and animals, each unit containing a predetermined quantity of active material calculated to produce sleep in association with the required pharmaceutical diluent, carrier, or vehicle. The specifications for the novel unit dosage forms of this invention are dictated by and directly dependent on (a) the unique characteristics of the active material and the particular effect to be achieved, and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, granules, wafers, cachets, teaspoonfuls, tablespoonfuls, dropperfuls, ampuls, vials, segregated multiples of any of the foregoing, and other forms as herein described.

The dosage of the compound for treatment depends on route of administration, the age, weight, and condition of the patient. The dosage to be administered is calculated on the basis of from about 0.1 to about 1 mg./kg. weight of subject/day.

The compound is compounded with a suitable pharmaceutical carrier in unit dosage form for convenient and effective administration. In the preferred embodiments of this invention, the dosage units contain the compound in: 0.5, 1, 10, 25, 50, and 100 mg. amounts for systemic treatment: and 0.5% to 5% w/v for parenteral treatment.

The following examples are illustrative of the best mode contemplated by the inventor for carrying out his invention and are not to be construed as limiting.

EXAMPLE 1

A lot of 10,000 tablets, each containing 0.5 mg. of 8-chloro-1-[(dimethylamino)methyl]-6-phenyl-4H-s-triazolo[4,3-a][1,4]benzodiazepine is prepared from the following types and amounts of ingredients:

| | |
|---|---|
| 8-chloro-1-[(dimethylamino)methyl]-6-phenyl-4H-s-triazolo[4,3-a][1,4]benzodiazepine | 5 gm. |
| Dicalcium phosphate | 1,500 gm. |
| Methylcellulose, U.S.P. (15 cps.) | 60 gm. |
| Talc | 150 gm. |
| Corn Starch | 200 gm. |
| Calcium stearate | 12 gm. |

The benzodiazepine and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and stearate, and compressed into tablets.

These tablets are useful for treatment of anxiety and depression at a dose of 2–4 tablets a day.

EXAMPLE 2

One thousand two-piece hard gelatin capsules, each containing 1 mg. of 8-chloro-1-[(dimethylamino)methyl]-6-phenyl-4H-s-triazolo[4,3-a][1,4]benzodiazepine are prepared from the following types and amounts of ingredients:

| | |
|---|---|
| 8-chloro-1-[(dimethylamino)methyl]-6-phenyl-4H-s-triazolo[4,3-a][1,4]benzodiazepine | 1 gm. |
| Talc | 25 gm. |
| Magnesium stearate | 250 gm. |

The ingredients are mixed well and filled into capsules of the proper size.

Capsules so prepared are useful for treatment of anxiety and depression at a dose of 1 capsule four times a day.

EXAMPLE 3

One thousand tablets for sublingual use are prepared from the following ingredients:

| | |
|---|---|
| 8-chloro-1-[(dimethylamino)methyl]-6-phenyl-4H-s-triazolo[4,3-a][1,4]benzodiazepine | 10 gm. |
| Polyethylene glycol, 4,000 powdered | 150 gm. |
| Polyethylene glycol, 6,000 powdered | 75 gm. |

The ingredients are mixed well and compressed into sublingual-type tablets weighing 235 mg.

These tablets placed under the tongue are useful in the rapid induction of treatment for anxiety and depression at a dose of 1 tablet 4 times a day.

EXAMPLE 4

Soft gelatin capsules for oral use, each containing 10 mg. of 8-chloro-1-[(dimethylamino)methyl]-6-phenyl-4H-s-triazolo[4,3-a][1,4]benzodiazepine are prepared by first dispersing the micronized compound in corn oil to render the material capsulatable and then encapsulating in the usual manner.

One capsule taken daily is useful for anxiety and depression.

EXAMPLE 5

One thousand tablets, each containing 25 mg. of 8-chloro-1[(dimethylamino)methyl]-6-phenyl-4H-s-triazolo[4,3-a][1,4]benzodiazepine are made from the following types and amounts of ingredients:

| | |
|---|---|
| 8-chloro-[(dimethylamino)methyl]-6-phenyl-4H-s-triazolo[4,3-a][1,4]benzodiazepine | 25 gm. |
| Lactose | 355 gm. |
| Microcrystalline cellulose HF | 100 gm. |
| Starch | 16 gm. |
| Magnesium stearate powder | 4 gm. |

The ingredients are screened and blended together and pressed into 500 mg. tablets.

The tablets are useful for treating anxiety and depression at a dose of 1 tablet 3 times a day.

EXAMPLE 6

A sterile preparation suitable for intramuscular injection and containing 10 mg. of 8-chloro-1-[(dimethylamino)methyl]-6-phenyl-4H-s-triazolo[4,3-a][1,4]benzodiazepine in each milliliter is prepared from the following ingredients:

| | |
|---|---|
| 8-chloro-1-[(dimethylamino)methyl]-6-phenyl-4H-s-triazolo[4,3-a][1,4]benzodiazepine | 10 gm. |
| Benzyl benzoate | 2 ml. |
| Methylparaben | 1.5 gm. |
| Propylparaben | 0.5 gm. |
| Cottonseed oil q.s. | 1,000 ml. |

One milliliter of this sterile preparation is injected for treatment of neurotic depression.

EXAMPLE 7

One thousand tablets, each containing 50 mg. of 8-chloro-1[(dimethylamino)methyl]-6-phenyl-4H-s-triazolo[4,3-a][1,4]benzodiazepine methanesulfonate are made from the following types and amounts of ingredients:

| | |
|---|---|
| 8-chloro-1[(dimethylamino)methyl]-6-phenyl-4H-s-triazolo[4,3-a][1,4]benzodiazepine methanesulfonate | 50 gm. |
| Lactose | 330 gm. |
| Microcrystalline cellulose NF | 100 gm. |
| Starch | 16 gm. |
| Magnesium stearate powder | 4 gm. |

The ingredients are screened and blended together and pressed into 500 mg. tablets.

The tablets are useful for treating neurotic depression at a dose of 1 tablet 3 times a day.

EXAMPLE 8

One thousand two-piece hard gelatin capsules, each containing 100 mg. of 8-chloro-1-[(dimethylamino)methyl]-6-phenyl-4H-s-triazolo[4,3-a][1,4]benzodiazepine are prepared from the following types and amounts of ingredients:

| | |
|---|---|
| 8-chloro-1-[(dimethylamino)methyl]-6-phenyl-4H-s-triazolo[4,3-a][1,4]benzodiazepine | 100 gm. |
| Talc | 25 gm. |
| Magnesium stearate | 250 gm. |

The ingredients are mixed well and filled into capsules of the proper size.

Capsules so prepared are useful to reduce anxiety and depression in adults at a dose of one to three capsules daily.

EXAMPLE 9

A sterile aqueous solution for parenteral administration containing 25 mg. of 8-chloro-1-[(dimethylamino)methyl]-6-phenyl-4H-s-triazolo[4,3-a][1,4]benzodiazepine methanesulfonate in each 1 ml., is prepared from the following types and amounts of ingredients:

| | |
|---|---|
| 8-chloro-1-[(dimethylamino)methyl]-6-phenyl-4H-s-triazolo[4,3-a][1,4]benzodiazepine methanesulfonate | 25 gm. |
| Water for injection q.s. | 1000 ml. |

The active ingredient is dissolved in the water for injection and the solution sterilized by filtration. The sterile solution is filled into 1 ml. sterile vials and sealed.

The composition is useful for treating anxiety and depression at a dose of 1 to 2 ml. daily.

EXAMPLE 10

One thousand ml. of an elixir, containing 100 mg. of 8-chloro-1-[(dimethylamino)methyl]-6-phenyl-4H-s-triazolo-[4,3-a][1,4]benzodiazepine methanesulfonate in each 5 ml. is prepared from the following types and amounts of ingredients:

| | | |
|---|---|---|
| 8-chloro-1-[(dimethylamino)methyl]-6-phenyl-4H-s-triazolo[4,3-a][1,4]benzodiazepine methanesulfonate | 20 | gm. |
| Citric acid | 0.1 | gm. |
| F.D.C. Red No 1 | 0.04 | gm. |
| Saccharin | 0.1 | gm. |
| Sucrose | 200.0 | gm. |
| Oil of spearmint | 0.1 | gm. |
| Oil of Wintergreen | 0.1 | gm. |
| Polysorbate to U.S.P. | 1.0 | gm. |
| Ethanol 95% | 200.0 | ml. |
| Glycerin | 150.0 | ml. |
| Water q.s. | 1,000.0 | ml. |

The sugar is dissolved in 450 ml. of water and the citric acid, color and the 8-chloro-1-[(dimethylamino)methyl]-6-phenyl-4H-s-triazolo[4,3-a][1,4]benzodiazepine methanesulfonate added thereto. The saccharin is added to the mixture of alcohol and glycerin and stirred until dissolved. The flavors are mixed with the polysorbate 80 and added to the alcohol-glycerin solution followed by the addition of the sugar solution and sufficient water to make 1,000 ml.

The elixir is useful in the treatment of anxiety and depression at a dose of 1 to 2 teaspoons a day.

EXAMPLE 11

Following the procedure of the preceding Examples 1 through 8, inclusive, unit dosage forms are similarly prepared substituting an equal amount each of 8-chloro-1-[aminomethyl]-6-phenyl-4H-s-triazolo[4,3-a][1,4]benzodiazepine, 8-chloro-1-[(methylamino)methyl]-6-phenyl-4H-s-triazolo[4,3-a][1,4]benzodiazepine, 8-chloro-1-[(ethylmethylamino)methyl]-6-phenyl-4H-s-triazolo[4,3-a][1,4]benzodiazepine, 8-chloro-1-[(diethylamino)methyl]-6-phenyl-4H-s-triazolo[4,3-a][1,4]benzodiazepine, 8-bromo-1-[(dimethylamino)methyl]-6-phenyl-4H-s-triazolo[4,3-a][1,4]benzodiazepine, 8-bromo-1-[(methylamino)methyl]-6-phenyl-4H-s-triazolo-[4,3-a][1,4]benzodiazepine, 8-trifluoromethyl-1-[(amino)methyl]-6-phenyl-4H-s-triazolo[4,3-a][1,4]benzodiazepine, 8-bromo-1-[(diethylamino)methyl]-6-phenyl-4H-s-triazolo[4,3-a][1,4]benzodiazepine, 8-bromo-1-[(ethylmethylamino)methyl]-6-phenyl-4H-s-triazolo[4,3-a][1,4]benzodiazepine, 8-fluoro-1-[(dimethylamino)methyl]-6-phenyl-4H-s-triazolo[4,3-a][1,4]benzodiazepine, 8-fluoro-1-(aminomethyl)-6-phenyl-4H-s-triazolo[4,3-a][1,4]benzodiazepine, 8-cyano-1-[(methylamino)methyl]-6-phenyl-4H-s-triazolo[4,3-a][1,4]benzodiazepine, 8-nitro-1-[(dimethylamino)methyl]-6-phenyl-4H-s-trizolo[4,3-a][1,4]benzodiazepine, and 8-(methylthio)-1-(aminomethyl)-6-phenyl-4H-s-triazolo[4,3-a][1,4]benzodiazepine for the 8-chloro-1-[(dimethylamino)methyl]-6-phenyl-4H-s-triazolo[4,3-a][1,4]benzodiazepine.

I claim:

1. A pharmaceutical composition for reducing anxiety and depression comprising, in unit dosage form, from about 0.5 to about 100 mg. of a compound of the formula:

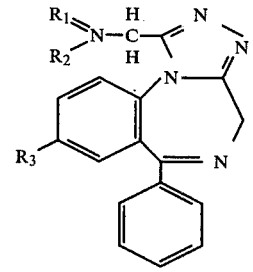

wherein $R_1$ and $R_2$ are hydrogen, methyl or ethyl, and $R_3$ is hydrogen, fluorine, chlorine, bromine, —CN, —NO$_2$, —CF$_3$, or alkylthio in which the alkyl is from one to three carbon atoms, inclusive, including the pharmacologically acceptable acid addition salt or N-oxide thereof, in association with a pharmaceutical carrier.

2. The composition of claim 1 wherein the compound is 8-chloro-1-[(dimethylamino)methyl]-6-phenyl-4H-s-triazolo[4,3-a][1,4]benzodizepine.

3. The composition of claim 1 wherein the compound is 8-fluoro-1-[(dimethylamino)methyl]-6-phenyl-4H-s-triazolo[4,3-a][1,4]benzodiazepine.

4. The composition of claim 1 wherein the compound is 8-chloro-1-[(dimethylamino)methyl]-6-phenyl-4H-s-triazolo[4,3-a][1,4]benzodiazepine methanesulfonate.

5. The composition of claim 1 wherein the compound is 8-chloro-1-(aminomethyl)-6-phenyl-4H-s-triazolo[4,3-a][1,4]benzodiazepine.

6. The composition of claim 1 wherein the compound is 8-chloro-1-[(methylamino)methyl]-6-phenyl-4H-s-triazolo[4,3-a][1,4]benzodiazepine.

7. The composition of claim 1 wherein the compound is 8-trifluoromethyl-1-[(dimethylamino)methyl]-6-phenyl-4H-s-triazolo[4,3-a][1,4]benzodiazepine.

8. The composition of claim 1 wherein the compound is 8-nitro-1-[(dimethylamino)methyl]-6-phenyl-4H-s-triazolo[4,3-a][1,4]benzodiazepine.

9. A process for reducing anxiety and depression comprising the administration to a human or animal subject an effective amount of a compound of the formula:

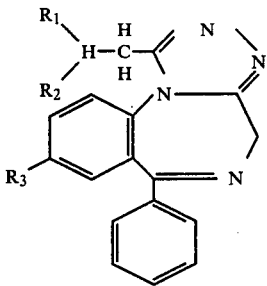

wherein $R_1$ and $R_2$ are hydrogen, methyl or ethyl, and $R_3$ is hydrogen, fluorine, chlorine, bromine, —CN, —NO$_2$, —CF$_3$, or alkylthio in which the alkyl is from one to three carbon atoms, inclusive, including the pharmacologically acceptable acid addition salt or N-oxide thereof, in association with a pharmaceutical carrier.

10. The process of claim 9 wherein from about 0.1 mg./kg./day to about 1 mg./kg./day of the compound is administered.

11. The process of claim 10 wherein the compound is 8-chloro-1[(dimethylamino)methyl]-6-phenyl-4H-s-triazolo[4,3a][1,4]benzodiazepine.

12. The process of claim 10 wherein the compound is 8-fluoro-1-[(dimethylamino)methyl]-6-phenyl-4H-s-triazolo[4,3-a][1,4]benzodiazepine.

13. The process of claim 10 wherein the compound is 8-chloro-1-[(dimethylamino)methyl]-6-phenyl-4H-s-triazolo[4,3-a][1,4]benzodiazepine methanesulfonate.

14. The process of claim 10 wherein the compound is 8-chloro-1-(aminomethyl)-6-phenyl-4H-s-triazolo[4,3-a][1,4]benzodiazepine.

15. The process of claim 10 wherein the compound is 8-chloro-1-[(methylamino)methyl]-6-phenyl-4H-s-triazolo[4,3-a][1,4]benzodiazepine.

16. The process of claim 10 wherein the compound is 8-trifluoromethyl-1-[(dimethylamino)methyl]-6-phenyl-4H-s-triazolo[4,3-a][1,4]benzodiazepine.

17. The process of claim 10 wherein the compound is 8-nitro-1-[(dimethylamino)methyl]-6-phenyl-4H-s-triazolo[4,3-a][1,4]benzodiazepine.

* * * * *

UNITED STATES PATENT AND TRADEMARK OFFICE
CERTIFICATE OF CORRECTION

PATENT NO. : 4,264,615
DATED : April 28, 1981
INVENTOR(S) : Jackson B. Hester, Jr.

It is certified that error appears in the above—identified patent and that said Letters Patent is hereby corrected as shown below:

Column 4, line 18, "cellulose HF" should read -- cellulose NF --.
Column 5, line 54, "Polysorbate to" should read -- Polysorbate 80 --.
Column 6, line 27, "trizolo" should read -- triazolo --.
Column 7, line 17, should appear as follows intead of as in the patent:

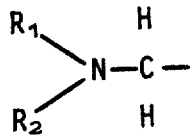

Signed and Sealed this

Fourteenth Day of July 1981

[SEAL]

Attest:

GERALD J. MOSSINGHOFF

Attesting Officer

Commissioner of Patents and Trademarks